(12) United States Patent
Panescu

(10) Patent No.: US 6,790,206 B2
(45) Date of Patent: Sep. 14, 2004

(54) COMPENSATION FOR POWER VARIATION ALONG PATIENT CABLES

(75) Inventor: Dorin Panescu, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/066,054

(22) Filed: Jan. 31, 2002

(65) Prior Publication Data

US 2003/0144655 A1 Jul. 31, 2003

(51) Int. Cl.⁷ .............................................. A61B 18/18
(52) U.S. Cl. .................................. 606/34; 606/42
(58) Field of Search .................... 606/32, 34, 35, 606/38–42

(56) References Cited

U.S. PATENT DOCUMENTS

| | | | | |
|---|---|---|---|---|
| 3,601,126 A | * | 8/1971 | Estes | 606/35 |
| 4,785,815 A | | 11/1988 | Cohen | |
| 4,945,912 A | | 8/1990 | Langberg | |
| 5,167,658 A | * | 12/1992 | Ensslin | 606/34 |
| 5,500,012 A | * | 3/1996 | Brucker et al. | 607/122 |
| 5,540,681 A | * | 7/1996 | Strul et al. | 606/34 |
| 5,542,916 A | | 8/1996 | Hirsch et al. | |
| 5,769,846 A | | 6/1998 | Edwards et al. | |
| 5,772,659 A | * | 6/1998 | Becker et al. | 606/34 |
| 5,817,093 A | * | 10/1998 | Williamson et al. | 606/50 |
| 5,868,737 A | | 2/1999 | Taylor et al. | |
| 5,947,964 A | * | 9/1999 | Eggers et al. | 606/41 |
| 5,957,920 A | * | 9/1999 | Baker | 606/33 |
| 5,957,969 A | | 9/1999 | Warner et al. | |
| 6,004,269 A | | 12/1999 | Crowley et al. | |
| 6,193,713 B1 | | 2/2001 | Geistert et al. | |
| 6,197,023 B1 | | 3/2001 | Muntermann | |
| 6,203,493 B1 | * | 3/2001 | Ben-Haim | 600/117 |
| 6,241,724 B1 | | 6/2001 | Fleischman et al. | |
| 6,271,508 B1 | | 8/2001 | Thompson et al. | |
| 6,287,303 B1 | | 9/2001 | Geistert et al. | |

\* cited by examiner

*Primary Examiner*—Michael Peffley
(74) *Attorney, Agent, or Firm*—Bingham McCutchen LLP

(57) ABSTRACT

A method and system for delivering power over a patient cable to a therapeutic device, in which a variable that depends on the delivered power is sensed or measured near a distal end of the patient cable, and a feedback signal is generated based on the sensed or measured value. The delivered power is adjusted based at least in part on the feedback signal to compensate for power variance along the patient cable.

35 Claims, 3 Drawing Sheets

COMPENSATION FOR POWER VARIATION ALONG PATIENT CABLES

BACKGROUND OF THE INVENTION

1. Field of the Invention

The field of the invention is power generators for medical and therapeutic devices, and, more particularly, power generator control for medical and therapeutic devices.

2. Background of the Invention

The power generators for many medical and therapeutic devices, such as those used in ablative therapy, are generally remotely located from the devices. A patient cable is typically provided to electrically couple the power generator to the therapeutic device. When the length of the patient cable is long, either because of design, or because doctors or nurses extend the original length of the patient cable, the power along the patient cable can vary significantly, causing the energy delivered by the therapeutic device to be inaccurate.

In ablative therapy, targeted biological tissue is heated by a therapeutic device to create lesions. The creation of lesions in cardiac tissue, for example, is used to treat cardiac arrhythmia by preventing the propagation of electrical signals across each lesion. The energy delivered by these therapeutic devices can be in a form of ultrasound, to heat with sonic energy, radio frequency or microwave, to heat with electromagnetic field energy, or induction heating, to heat with magnetic field energy, as is known in the art. In one example, the therapeutic device includes one or more electrodes for delivering radio frequency energy. See for example, U.S. Pat. No. 6,241,724B1 and U.S. Pat. No. 6,004,269, which are incorporated by reference herein.

It is important that an accurate amount of energy be delivered to the target tissue to create the desired lesions. Delivery of less energy than expected may prevent the targeted biological tissue from being sufficiently heated to achieve the desired lesion creation. Delivery of an excess amount of energy could cause excess lesion formation.

Power loss along the patient cable may be caused by a variety of factors, including the resistance of the wire in the patient cable, the geometry of the cable (i.e., whether it is coiled or stretched), and any electrical coupling to conductive features of the surroundings, such as steel floor, pipes, and walls. The power loss could fluctuate during an operation of a therapeutic device, depending on these factors. In addition, it is a common practice to extend the length of patient cables with extension cords. The length, geometry, and electrical characteristics of the extension cords, as well as the connection between the extension cord and the patient cable, and between extension cords, could also cause power loss along the extended patient cable.

Power loss along the patient cable may become noticeable when the patient cable length reaches ten (10) feet, or sometimes even less, depending on other factors as described previously. The power loss could become significant when the patient cable length reaches about fifty (50) feet. The uncertain nature of most of the factors causing power loss discussed above (i.e., the geometry of the patient cable, the surrounding environment in which the cable is placed, and the type of extension cords) makes it difficult to calculate power variance along the patient cable. It is therefore difficult to accurately regulate the power output of a therapeutic device to compensate for the variance of the power along the cable.

It would be advantageous to be able to accurately compensate for power variance along the patient cable so that a desired amount energy is delivered to a therapeutic device connected to the patient cable.

SUMMARY OF THE INVENTION

According to the present invention, a characteristic of the power provided to a therapeutic device through a patient cable, or a characteristic of the energy delivered by the therapeutic device, or both, is sensed. A feedback signal is provided based on the sensed value to adjust the power generated by a power generatorSJ-39249.1, if necessary, so that the therapeutic device delivers a desired amount of energy.

In one embodiment, a system for delivering power to a therapeutic device comprises a generator including a power regulation circuit for producing an output power at a generator output. A patient cable is provided having a proximal end configured for coupling to the generator output and a distal end configured for coupling to the therapeutic device. A feedback apparatus is coupled to one or both of the patient cable and the therapeutic device proximate the distal end of the patient cable. The feedback apparatus is configured to sense or measure a variable that depends on a delivered power and to generate a feedback signal depending on the delivered power. The power regulation circuit controls the output power of the generator, based at least in part on the feedback signal. Methods for delivering power to a therapeutic device are also disclosed.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals.

DETAILED DESCRIPTION OF THE PREFERRED EMBODIMENTS

Figure 1:
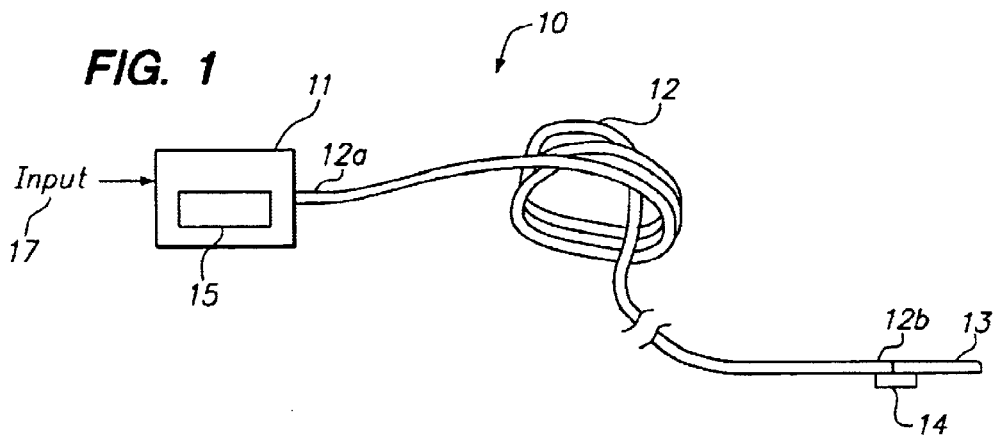
FIG. 1 illustrates a system for delivering power to a therapeutic device in accordance with the present invention.

FIG. 1 illustrates a system 10 for delivering power to a therapeutic device 13, such as that used in ablative therapy, according to the present invention. The system includes a power generator 11, a patient cable 12, and a feedback apparatus 14. The patient cable 12 is coupled to an output of the generator 11 at a proximal end 12a of the cable 12, and the patient cable 12 is coupled to the therapeutic device 13 at a distal end 12b of the patient cable 12.

The power generator 11 has an input 17 for selecting a desired power. The power generator 11 includes a power regulation circuit 15, such as a microprocessor, located inside, or electrically connected to the power generator 11, for regulating the generated power. The power generator 11 may be a RF generator, for example.

The feedback apparatus 14 is preferably located near the distal end of the patient cable 12, and can be electrically connected to the patient cable 12, to the therapeutic device 13, or to both. The feedback apparatus 14 senses or measures a variable that depends on the power near the end of the patient cable 12 (or the power itself), or a variable that depends on the energy delivered by the therapeutic device 13, as discussed further below. As used here, "measure" means to determine a magnitude of a variable. The feedback apparatus 14 then provides a feedback signal to the power regulation circuit 15 based on the sensed or measured value. The power regulation circuit 15 then adjusts the generated power based at least in part on the feedback signal, if necessary.

Figure 2A:
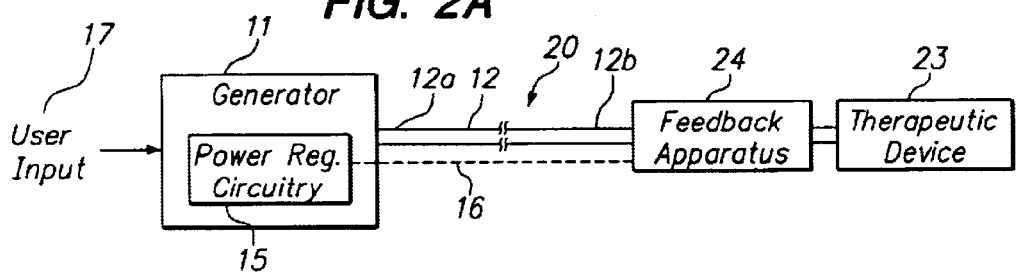
FIG. 2A illustrates a system for delivering power to a therapeutic device in which the feedback apparatus is connected to the patient cable, in accordance with one embodiment of the present invention.

FIG. 2A illustrates a system 20 in accordance with one embodiment of the invention, where a feedback apparatus 24 is electrically connected to the patient cable 12 near the distal end 12b of the cable 12. The feedback apparatus 24 is configured to sense or measure one or more variables that depend on a characteristic of the power delivered to the therapeutic device, such as voltage, current, heat, frequency, or the power itself. The feedback apparatus 24 is preferably located as close to the therapeutic device 23 as possible in order to achieve the optimum benefit of the present invention. Where the patient cable 12 is about fifty (50) feet, for example, the feedback apparatus 24 is preferably located within about three (3) feet or less of the therapeutic device 23. However, depending on the total length of the patient cable 12, the feedback apparatus 24 can be located further away from the therapeutic device 23 without significantly losing the benefit of the present invention.

A feedback path 16 is shown in phantom between the feedback apparatus 24 and the power generator 11. The feedback path 16 is a way of physically delivering the feedback signal to the power generator 11. In one example, the feedback path 16 comprises at least one wire connecting the feedback apparatus 24 to the power generator 11 for transmission of the feedback signal from the feedback apparatus 24 to the power generator 11. In an alternative example, the feedback path 16 comprises optical cable. In yet another example, the feedback path 16 comprises a wireless transmitter that transmits the feedback signal to a receiver electrically coupled to the power generator 11 in the form of radio frequency signals.

To use the system 20 of FIG. 2A, a user initially enters an input 17, such as a power input, associated with a desired power to be delivered to the therapeutic device 23. The user input 17 may be a desired delivered power or a variable associated with a desired delivered power such as temperature, for example.

Based on the user's input 17, the power generator 11 generates a power and delivers the power over the patient cable 12. The feedback apparatus 24 senses or measures the one or more variables of the power, or the power itself, as discussed above. Based on the sensed or measured value, the feedback apparatus 24 generates a feedback signal, which can be either digital or analog, and transmits the feedback signal via the feedback path 16 to the power generator 11 at the proximal end 12a of the patient cable 12. The actual measurement of the sensed variable can be performed by the feedback apparatus 24, by the power generator 11, or by a power regulation circuit 15.

Once the feedback signal is transmitted to the power generator 11, the power regulation circuit 15 processes the feedback signal and adjusts a characteristic of the output power generated by the power generator 11 such that the delivered power better matches the desired power associated with the user's input 17, if necessary. The characteristic of the output power could be the amplitude, for example. This ensures that the desired power is being delivered to the therapeutic device 23 at the distal end of the patient cable 12. In ablative therapy, for example, the system 20 for delivering power to the therapeutic device helps achieve the desired degree of the lesion creation.

Figure 2B:
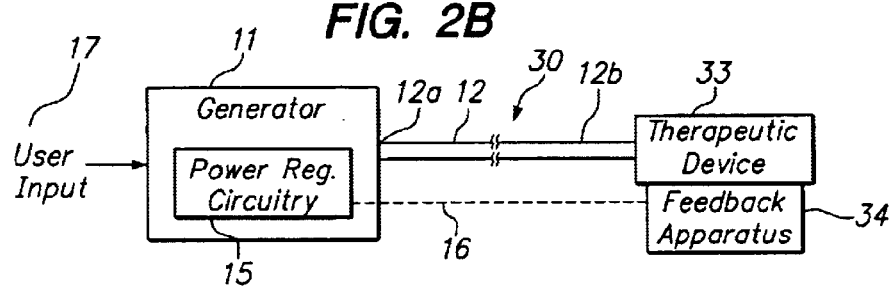
FIG. 2B illustrates a system for delivering power to a therapeutic device in which the feedback apparatus is connected to the therapeutic device in accordance with another embodiment of the present invention.

FIG. 2B illustrates a system 30 in accordance with another embodiment of the present invention, where the feedback apparatus 34 is connected to the therapeutic device 33. Although the feedback apparatus 34 is shown to be attached adjacent to the outside of the therapeutic device 33, it is not so limited. The feedback apparatus 34 can be connected to the therapeutic device 33 via a cable, or located inside the therapeutic device 33, for example. As described above, the feedback apparatus 34 is configured to sense or measure at least one variable that depends on the power delivered to the therapeutic device 33, or the power itself. Alternatively, since the feedback apparatus is proximate the therapeutic device 33, the feedback apparatus 34 can also be configured to sense or measure a variable that depends on the amount of energy being delivered by the therapeutic device 33. For example, the feedback apparatus 34 can be configured to sense or measure sonic energy or heat, which are dependent on the amount of power delivered to the therapeutic device 33, as is known in the art.

Figure 2C:
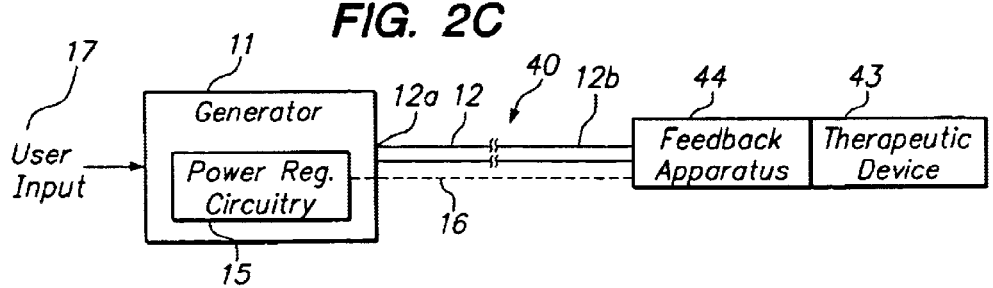
FIG. 2C illustrates a system for delivering power to a therapeutic device in which the feedback apparatus is connected to both the patient cable and the therapeutic device in accordance with yet another embodiment of the present invention.

FIG. 2C illustrates a system 40 in accordance with another embodiment of the present invention. As shown in FIG. 2C, where the feedback apparatus 44 is connected to both the patient cable 12 and the therapeutic device 43. As in FIG. 2B, the feedback apparatus 44 in FIG. 2C can be configured to sense or measure at least one variable that depends on a characteristic of the delivered power at the therapeutic device 43 or the power itself. As in the embodiment of FIG. 2B, since the feedback apparatus 44 is close to the therapeutic device, the feedback apparatus 44 can also be configured to sense or measure a variable that depends on the amount of energy being delivered by the therapeutic device 43, such as sonic energy or heat, as described above.

Figure 3:
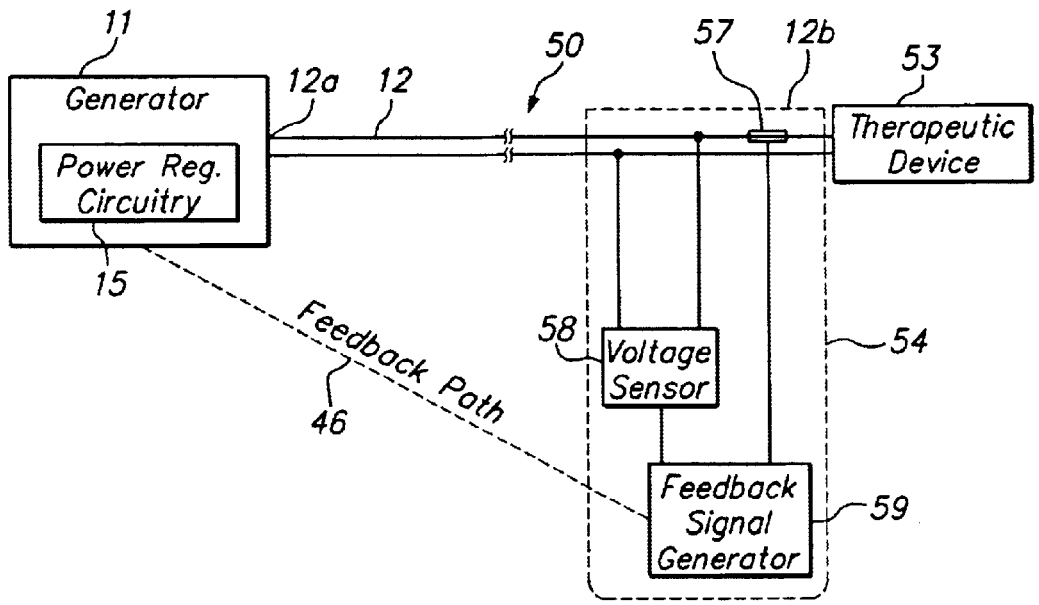
FIG. 3 illustrates a system for delivering power to a therapeutic device in which the feedback apparatus comprises a voltage sensor and a current sensor, according to a preferred embodiment of the present invention.

FIG. 3 illustrates a system 50 where the feedback apparatus 54 comprises a current sensor 57 and a voltage sensor 58, in accordance with a preferred embodiment of the present invention. For example, the current and the voltage sensors may be implemented using current and voltage transformers, respectively. The current sensor 57 and the voltage sensor 58 sense or measure the current and the voltage, respectively, near the distal end 12b of the patient cable 12. Although the feedback apparatus 54 is shown to be electrically connected to the patient cable 12, it can be connected to the therapeutic device 53 only, or to both the patient cable 12 and the therapeutic device 53 as well, as in the embodiments of FIGS. 2B–2C. Since power is a function of voltage and current, the delivered power near the distal end 12b of the patient cable 12 can be determined based on the voltage and current measurements.

A feedback signal generator 59 is electrically coupled to the current sensor 57 and the voltage sensor 58. Based on the sensed voltage and current, the feedback signal generator 59 generates a feedback signal, and transmits the feedback signal to the power generator 11. In one variation, the feedback signal generator 59 processes the voltage and current information to determine the value of the delivered power and then generates a feedback signal associated with the delivered power. In another variation, the feedback signal contains the voltage or current information and the power regulation circuit 15 processes the voltage or the current information to determine the power delivered near the distal end 12b of the patient cable 12 based at least in part on the feedback signal to ensure that the desired amount of power is being delivered to the therapeutic device 53. In yet another variation, the feedback generator 59 transmits the sensed variable to the generator 11. The generator 11 then measures the sensed variable and provides the measurement to the power regulation circuit 15.

Alternatively, only the voltage or current sensor may be used. In an alternative embodiment, the current loss along the patient cable 12 is assumed to be negligible. As a result, the current near the distal end 12b of the patient cable 12 is assumed to be the same as the current at the proximal end 12a of the patient cable 12, which can be determined based on the current inside the power generator 11. In this embodiment, the feedback apparatus is configured to measure only the voltage near the distal end of the patient cable 12. Since power is a function of voltage and current, the delivered power near the distal end 12b of the patient cable 12 can be determined based on the voltage measurement near the distal end 12b of the patient cable 12 and the current measured at the power generator 11.

Figure 4:
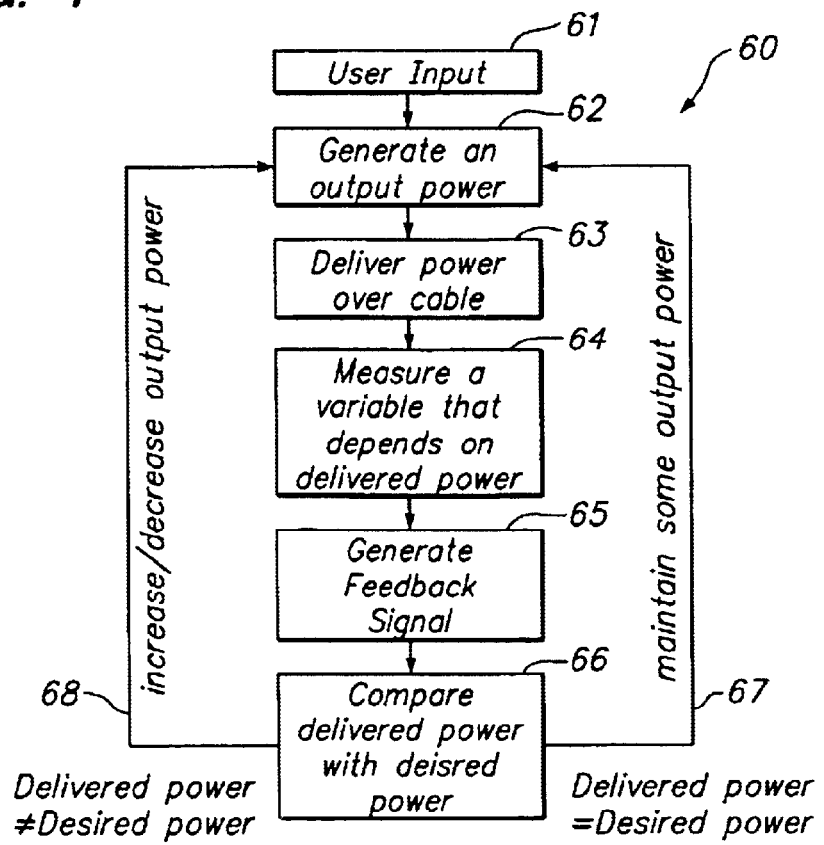
FIG. 4 is a flow chart of a process for compensating for power variance near the distal end of a patient cable according to an embodiment of the present invention.

FIG. 4 is a flow chart illustrating a process 60 for compensating for power losses. First, a user enters an input associated with a desired power to be delivered to a therapeutic device (step 61). Based on the user's input, an output power is generated (step 62). As discussed previously, the user input may be a desired delivered power, or a variable associated with a desired delivered power such as temperature, for example. The output power is then delivered (step 63) over a patient cable to a therapeutic device. The therapeutic device delivers an amount of energy based on the power delivered to the therapeutic device. As discussed above, in the example of ablative therapy, the energy delivered by the therapeutic device may be in a form of radio frequency, ultrasound, microwave, or heat, for examples.

In step 64, a variable that depends on a characteristic of the delivered power is sensed near the distal end of the patient cable. In one example, the sensed variable is measured by the feedback apparatus. Alternatively, the sensed variable is transmitted to the generator and the sensed variable is measured at the generator.

In one embodiment, the measured variable depends on the power delivered to the therapeutic device, such as voltage, current, power, etc. Alternatively, the measured variable may also depend on the energy delivered by the therapeutic device to the target tissue such as temperature or ultrasound energy.

Based on the sensed or measured variable obtained in step 64, a feedback signal is generated (step 65). The feedback signal can be analog or digital. In a preferred embodiment, the feedback signal is transmitted by a wire connected to the power generator, as discussed above. In another embodiment, the feedback signal is a form of radio frequency signal that is transmitted by a wireless device, as also discussed above. In yet another embodiment, the feedback signal is transmitted by an optical cable.

In step 66, the feedback signal associated with the delivered power is compared with the expected value associated with the desired power. The generated output power is then modified by a power regulation circuit based at least in part on the feedback signal such that the delivered power near the distal end of the patient cable better matches the desired power associated with the user's input in step 61. If the feedback signal indicates that the delivered power is less than the desired power associated with the user's input, the generated output power is then increased until the delivered power matches the desired power. If the feedback signal indicates that the delivered power is more than the desired power associated with the user's input, the generated output power is then decreased until the delivered power matches the desired power. This process ensures that the power delivered to the therapeutic device closely matches the desired amount of power. This is especially beneficial in ablative therapies in which accurate power delivery to the target tissue is necessary in order to achieve the desired lesion creation.

Preferably, the method 60 continuously or periodically monitors the delivered power and the generated power is continuously or periodically being adjusted, as necessary, as illustrated by the arrows 67 and 68, which complete the loop between steps 62 through 66. The generated power may also be adjusted once based on a single measurement in step 64 and the same adjusted power would be generated and delivered to the therapeutic device throughout a session or operation.

Figure 5:
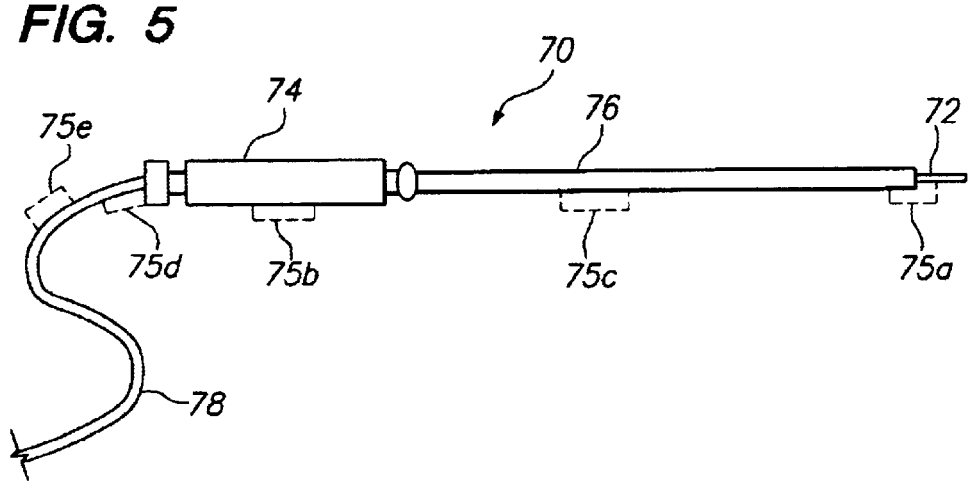
FIG. 5 shows an ablation catheter having a feedback apparatus, and various positions in which the feedback apparatus may be located.

The system of the present invention may be particularly useful in cardiac ablation systems, where the delivered power is critical in achieving the desired lesion creation. The therapeutic device 13, 23, 33, 43 may therefore be an ablation catheter, for example. Cardiac ablation catheters are described in U.S. Pat. No. 6,241,724B1 and U.S. Pat. No. 6,004,269, for example, which are incorporated by reference herein. FIG. 5 is an example of a cardiac ablation catheter 70 comprising a handle 74, a catheter shaft 76, and an electrode 72 at the distal end of the catheter shaft. A patient cable 78 is electrically coupled to a wire or wires (not shown) extending through the catheter shaft, to the electrode. Power provided from a generator 11, as in the systems above, is delivered to the electrode 72 through the wire or wires. A feedback apparatus 75 may be incorporated in the catheter 70 proximate the electrode 72 at the distal end of the catheter 70, on the handle 74 of the catheter 70, anywhere along the shaft 76 of the catheter 70, or on the patient cable 78 itself, preferably proximate to the handle 74. References 75a to 75e represent examples of various positions in which the feedback apparatus 75 may be located.

Although the embodiments above have been described in reference to therapeutic devices that deliver energy in a form of microwave, ultrasound, radio frequency, and heat, the scope of the invention is not so limited. The present invention also applies to medical devices that deliver other forms of energy, such as mechanical energy, to a patient. For example, medical devices that deliver mechanical energy for displacing biological tissue, such as medical clamps, or medical devices that deliver energy for cutting biological tissue, such as oscillation knives, can use the system described herein to ensure that the desired amount of force or pressure is being applied to the tissue. This ensures proper displacement or cutting of the tissue and prevents injury to the patient.

Furthermore, although several embodiments have been described in reference to power loss along the patient cable, the present invention is also applicable for compensating for power gain along the patient cable.

Thus, although several preferred embodiments have been shown and described, it would be apparent to those skilled in the art that many changes and modifications may be made thereunto without the departing from the scope of the invention, which is defined by the following claims and their equivalents.

What is claimed:

1. A system for delivering power to a therapeutic device, comprising:
    a generator including a power regulation circuit for producing an output power at a generator output;
    a patient cable having a proximal end configured for coupling to the generator output, and a distal end configured for coupling to a therapeutic device; and
    a feedback apparatus connected to the distal end of the patient cable, the feedback apparatus comprising a current sensor, and configured to generate a feedback signal based on a current sensed by the current sensor;
    wherein the power regulation circuit is configured to compensate for a power change along the patient cable by controlling the output power based at least in part on the feedback signal.

2. The system of claim 1, further comprising a feedback path coupled to the feedback apparatus for transmitting the feedback signal to the generator.

3. The system of claim 2, wherein the feedback path comprises at least one wire connected to the power generator.

4. The system of claim 2, wherein the feedback path comprises a wireless transmitter.

5. The system of claim 1, wherein the feedback signal is analog.

6. The system of claim 1, wherein the feedback signal is digital.

7. The system of claim 1, wherein the feedback apparatus further comprises a voltage sensor.

8. The system of claim 7, wherein the feedback apparatus is configured to generate a feedback signal based on a current sensed by the current sensor and a voltage sensed by the voltage sensor.

9. The system of claim 1, wherein the patient cable comprises an extension cord.

10. The system of claim 1, wherein the patient cable comprises a plurality of extension cords.

11. A method for delivering power to a therapeutic device, comprising:
    generating an output power;
    delivering the output power over a patient cable to a therapeutic device;
    sensing a current at a distal end of the patient cable or at the therapeutic device;
    generating a feedback signal based on the sensed current; and
    compensating for a power loss along the patient cable by modifying the generated output power based at least in part on the feedback signal.

12. The method of claim 11, wherein the sensing step comprises sensing a current at the distal end of the patient cable.

13. The method of claim 11, wherein the sensing step comprises sensing a current at the therapeutic device.

14. The method of claim 11, wherein the therapeutic device delivers radio frequency (RF) energy.

15. The method of claim 11, wherein the therapeutic device delivers microwave energy.

16. The method of claim 11, wherein the therapeutic device delivers ultrasound energy.

17. The method of claim 11, further comprising transmitting the feedback signal to a power generator that generates the output power.

18. The method of claim 17, wherein the transmitting step comprises using at least one wire to transmit the feedback signal.

19. The method of claim 17, wherein the transmitting step comprises using a wireless transmitter to transmit the feedback signal.

20. The method of claim 11, wherein the feedback signal is analog.

21. The method of claim 11, wherein the feedback signal is digital.

22. The method of claim 11, further comprising sensing a voltage at a distal end of the patient cable or at the therapeutic device.

23. The method of claim 22, wherein the feedback signal is generated based on the sensed current and the sensed voltage.

24. A system for delivering power to a therapeutic device, comprising:
    a generator including a power regulation circuit for producing an output power at a generator output;
    a patient cable having a proximal end configured for coupling to the generator output, and a distal end configured for coupling to a therapeutic device; and
    a feedback apparatus connected to the distal end of the patient cable, the feedback apparatus comprising a voltage sensor, and configured to generate a feedback signal based on a voltage sensed by the voltage sensor;
    wherein the power regulation circuit is configured to compensate for a power change along the patient cable by controlling the output power based at least in part on the feedback signal.

25. A method for delivering power to a therapeutic device, comprising:
    generating an output power;
    delivering the output power over a patient cable to a therapeutic device;
    sensing a voltage at a distal end of the patient cable or at the therapeutic device;
    generating a feedback signal based on the sensed voltage; and
    compensating for a power loss along the patient cable by modifying the generated output power based at least in part on the feedback signal.

26. The method of claim 25, wherein the sensing step comprises sensing a voltage at the distal end of the patient cable.

27. The method of claim 25, wherein the sensing step comprises sensing a voltage at the therapeutic device.

28. A therapeutic system, comprising:
    a therapeutic device;
    a generator including a power regulation circuit for producing an output power at a generator output;
    a patient cable having a proximal end coupled to the generator output, and a distal end coupled to the therapeutic device; and
    a feedback apparatus connected to the therapeutic device, the feedback apparatus comprising a current sensor, and is configured to generate a feedback signal based on a current sensed by the current sensor;

wherein the power regulation circuit is configured to compensate for a power loss along the patient cable by controlling the output power based at least in part on the feedback signal.

29. The system of claim 28, wherein the therapeutic device delivers radio frequency (RF) energy.

30. The system of claim 28, wherein the therapeutic device delivers microwave energy.

31. The system of claim 28, wherein the therapeutic device delivers ultrasound energy.

32. A therapeutic system, comprising:
   a therapeutic device;
   a generator including a power regulation circuit for producing an output power at a generator output;
   a patient cable having a proximal end coupled to the generator output, and a distal end coupled to the therapeutic device; and
   a feedback apparatus connected to the therapeutic device, the feedback apparatus comprising a voltage sensor, and is configured to generate a feedback signal based on a voltage sensed by the voltage sensor;
   wherein the power regulation circuit is configured to compensate for a power loss along the patient cable by controlling the output power based at least in part on the feedback signal.

33. The system of claim 32, wherein the therapeutic device delivers radio frequency (RE) energy.

34. The system of claim 32, wherein the therapeutic device delivers microwave energy.

35. The system of claim 32, wherein the therapeutic device delivers ultrasound energy.

* * * * *

UNITED STATES PATENT AND TRADEMARK OFFICE
CERTIFICATE OF CORRECTION

PATENT NO. : 6,790,206 B2
DATED : September 14, 2004
INVENTOR(S) : Dorin Panescu It is certified that error appears in the above-identified patent and that said Letters Patent is hereby corrected as shown below:

Column 2,
Line 11, replace "generatorSJ-39249.1," with -- generator, --

Signed and Sealed this

Nineteenth Day of April, 2005

JON W. DUDAS
*Director of the United States Patent and Trademark Office*